United States Patent [19]
Bareiss

[11] 4,344,421
[45] Aug. 17, 1982

[54] APPARATUS FOR THE FAST, PAINLESS TREATMENT OF VARICOSE ULCERS

[76] Inventor: Raoul Bareiss, 2, rue de la gare, 68 500 Saint Amarin, France

[21] Appl. No.: 162,617

[22] Filed: Jun. 24, 1980

[30] Foreign Application Priority Data

Jun. 29, 1979 [FR] France .................................. 79 17435

[51] Int. Cl.³ .............................................. A61H 1/00
[52] U.S. Cl. ................................... 128/24 R; 128/118
[58] Field of Search .................. 128/24 R, 38, 60, 64, 128/118, 344, 325

[56] References Cited

U.S. PATENT DOCUMENTS

| 893,021 | 7/1908 | Siebert, Jr. | 128/64 |
| 1,147,560 | 7/1915 | Shurtleff | 128/24 R |
| 2,427,546 | 9/1947 | Brooks | 128/118 |
| 3,369,721 | 8/1968 | Mencacci | 128/64 |

Primary Examiner—Richard C. Pinkham
Assistant Examiner—T. Brown
Attorney, Agent, or Firm—Nathaniel A. Humphries

[57] ABSTRACT

A varicose ulcer is treated by establishing over a variable and repetitive period of time a localized pressure at the level of the perforating varis to force the blood back to the deep venous system. The pressure is generated by means applied from the exterior to the interior of the dehiscence of the tissues occupied by the perforating varix and a device for carrying out the process.

3 Claims, 6 Drawing Figures

APPARATUS FOR THE FAST, PAINLESS TREATMENT OF VARICOSE ULCERS

BACKGROUND OF THE INVENTION

The invention relates to a mechanical device for the fast, painless treatment of varicose ulcers.

Varicose ulcers are sores which originate from cutaneous and sub-cutaneous necrosis in a region of a leg, generally the lower third, which is in a state of anoxia from stagnation of the blood in the capillaries caused by a blockage of the return venous circulation. Usually, one or more varices of the perforating type are found above an ulcer. These perforating varices are usually present in the form of venous ectasis which is clearly visible beneath the skin, During exploration of a varix by a finger, the finger sinks to the depth of the sub-cutaneous tissues. The pathological reflux of the venous blood from the depth of the periphery originates at the level of these "venous holes" which connect the peripheral venous circulation and the deep venous circulation, due to a valvular defect. This results in the establishment of peripheral venous hypertension causing the blockage of the capillary circulation which is responsible for the anoxia of the cutaneous and sub-cutaneous tissues situated in front of these perforating varices and which causes nercrosis. The only aetiological treatment for overcoming varicose ulcers lies in the elimination of the pathological reflux of the deep venous blood toward the peripheral venous blood, that is to say, in practice, the treatment of the perforating varices themselves.

With the exception of pharmaceutical means, the means hitherto employed for overcoming venous hypertension at the level of the ulcerated region are all of the same type and involve the establishment of elastic support using elastic stocking or bandages. This is clearly inadequate as it is not possible in this way to prevent reflux at the level of the perforating varices since this reflux is situated deeply relative to the cutaneous surface (see FIGS. 1a and 1b in the attached drawings). Moreover, sclerosis of the varices is effected in a blind manner and is difficult to apply to the patient suffering from a varicose ulcer. Finally, if the compression of the ulcer itself and of a small peri-ulcerous zone can possibly allow the venous obstruction to be removed, the cause, that is to say the perforating verix, is not being attacked directly and, furthermore, there is a risk of interfering with the capillary circulation due to this compression.

SUMMARY OF THE INVENTION

A principal object of the present invention is to provide a mechanical device for the fast, painless treatment of varicose ulcers.

A further object of the invention is to provide a method of treating ulcers.

Accordingly, a varicose ulcer is treated by applying repeatedly for a variable period of time, a localised pressure at the level of the perforating varix, so as to force the blood back to the drop system, the said pressure being generated by means applied from the exterior to the interior of the dehiscence of the tissues occupied by the perforating varix.

The pressure may be applied using, for example, a dressing made of a rubbery material, provided on its periphery with adhesive for fixing the dressing to a leg. At least the base of the dressing, that is the part which is to be arranged against the leg, is enveloped in a sealed manner by an impermeable film. A section of the dressing is provided with means permitting the injection of a liquid or a gas into the space formed between the base and the impermeable film.

In order to inject the liquid or the gas for establishing pressure between the dressing and the patient's leg, the dressing may be traversed by a syringe needle, the end of which terminates between the base of the dressing and the film surrounding it, preferably in a cavity made on the said surface to prevent the needle from perforating the external film.

After injection of the fluid using a syringe connected to the needle, the needle is withdrawn from the body of the dressing whose elasticity should be such that, merely due to the mechanical properties of the material constituting the dressing, the hole is blocked, thus preventing any of the injected fluid from issuing.

The peripheral adhesive applied to the base of the dressing, preferably on the periphery of the film surrounding it, can be of any known type or can optionally be replaced by an external adhesive tape, which has the disadvantage of distributing the forces originating from the establishment of the pressure in an irregular manner. It is also possible to design a special support stocking which is provided with orifices with eylets in which the dressing will fit, or any other equivalent device.

The film arranged round the base of the dressing must be impermeable to the injected fluid whether it is a gas or liquid, for obvious reasons. Generally speaking water will be injected. This film is fixed to the dressing in a manner known per se, for example by heat-sealing or crimping or by any other technique which produces an optimum seal at the level of the bond between the film and the dressing.

The body of the dressing can be of any size or shape, the constraints in this respect being linked, on the one hand, to the patient's discomfort caused by an excessively thick material and on the other hand, to the constraint that this thickness has to absorb the pressure established between the leg and dressing without deforming.

Finally, with regard to the injection of fluid which is to generate the pressure and which consequently causes the film surrounding the base of the dressing to be applied into the dehiscence of the tissues occupied by the varix, it is necessary to avoid piercing the external film at the moment of injection. For this purpose, it is possible to provide, for example, a stop on the needle or any other limiting device or device which will indicate that the needle is level with the base of the dressing, for example, a small stop placed between the base of the dressing and the external film surrounding it.

The dressing is applied with the legs raised, and may be worn all day and removed at night. To remove it, the needle merely has to be reintroduced, and the sac containing the fluid empties automatically. The treatment is repeated several days in succession, resulting in immediate elimination of the pain caused by anoxia as well as optimum healing of the ulcer in terms of time and of quality, which could not be achieved by the processes or devices of the prior art. Normal perfusion of the ulcerated zone is re-established in practice by the capillaries and thus the oxygenation which had been interrupted.

DESCRIPTION OF PREFERRED EMBODIMENT

Figure 1A:
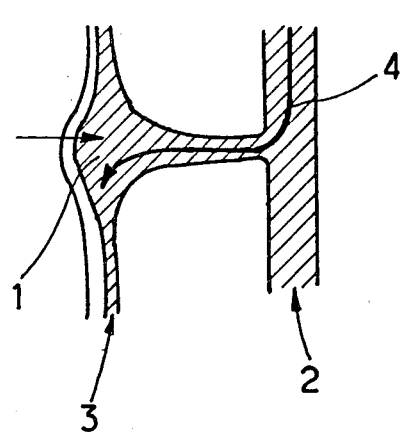
FIGS. 1a and 1b show the prior art diagrammatically.

FIG. 1a shows a perforating varix 1 arranged between the deep venous system 2 and the peripheral venous system 3. The arrow 4 shows the reflux of the blood from the deep system to the peripheral system.

Figure 1B:
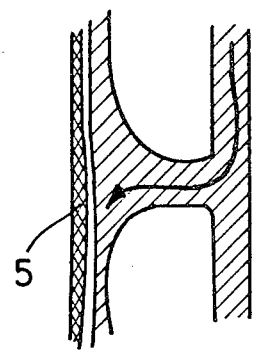
Figure 2:
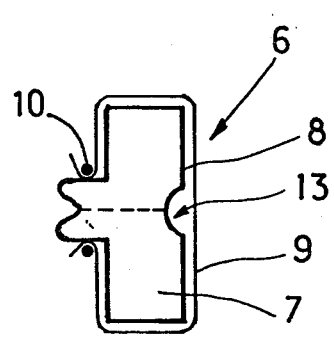
FIG. 2 is a sectional view of the device according to the invention ready to be applied to a leg.
Figure 3:
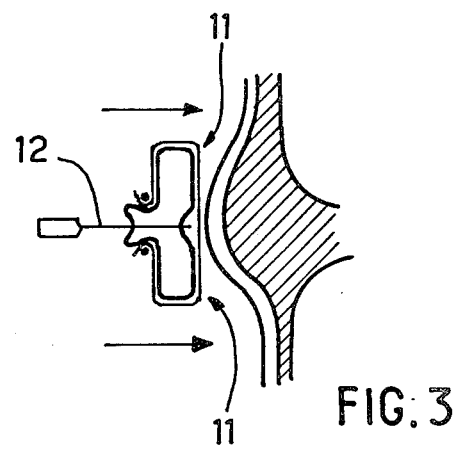
FIG. 3 is a sectional view of the device according to the invention applied to legs before establishment of the pressure.

FIG. 1b shows diagrammatically the action of an elastic support stocking 5. It is observed that the reflux inevitably persists with this uniform pressure.

The device according to the invention generally takes the form of a dressing in the form of a patch 6 comprising a body 7 whose base 8 is surrounded by a film 9 made, for example, of latex, the said film being fixed at 10 to the body 7 in a sealed manner.

A peripheral layer of adhesive 11 is arranged on the external face of the film 9. A needle 12 which merges, for example, into a cavity 13 made on the base 8 of the body of the patch is introduced into the central part of the body 7.

Figure 4:
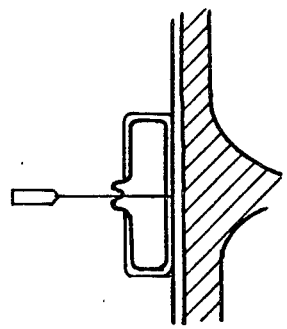
FIG. 4 is a sectional view of the device according to the invention applied to the leg but prior to the establishment of pressure.
Figure 5:
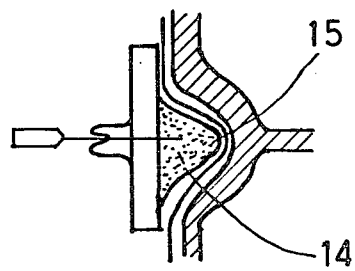
FIG. 5 is a sectional view of the device according to the invention applied to a leg after establishment of the pressure.

The device is applied to a leg (FIG. 4) where the adhesive holds it in place, and a fluid 14 is injected (FIG. 5) between the base of the body and the external film using a hypodermic syringe which is integral with the needle. This establishes a pocket of pressure 14 which forces the blood back to the deep system. In fact, this pocket protrudes into the dehiscence of the tissues occupied by the varix, matching the shape of this dehiscence.

This device should be applied to a raised leg to permit the varices to be emptied toward the deep venous system.

A separate device should be applied to each perforating varix.

Venous stasis of the varices is thus avoided by preventing reflux of the blood coloum from the deep system to the peripheral system, draining the region of the ulcer.

According to a preferred embodiment, the fluid could also be a mixture of a gas and a liquid, for example a mixture of air and water.

The application of this device can be extended to the treatment of all tropic cutaneous problems of venous origin and for stopping the development of a varicose network which is beginning.

What is claimed is:

1. A mechanical device for the ambulatory treatment of varicose ulcers, comprising a support body attached to the skin of the patient over the varicose ulcer, pressure establishing means on said support body for applying a continuous localized external inwardly applied pressure only in the area of the perforating varix for forcing the blood back to the deep venous system by the application of pressure applied from the exterior to the interior of the dehiscense of the tissues occupied by the perforating varix, wherein said support body includes a base portion, and further including an impermeable film overlying the base and peripherally sealed to the support body, a peripheral adhesive applied to external portions of the impermeable film overlying said base portion for holding the device on the leg skin of the patient and means traversing the body of the support body for injecting fluid between the base portion and the external film to cause the external film to bulge outwardly from the base portion to effect the application of pressure applied from the exterior to the interior of the dehiscense of the tissues occupied by the perforating varix.

2. A device according to claim 1 wherein the means for injecting fluid comprises a hypodermic syringe needle.

3. A device according to either claim 1 or claim 2 wherein said impermeable film is formed of latex.

* * * * *